US00PP27762P3

(12) United States Plant Patent
Bullis

(10) Patent No.: US PP27,762 P3
(45) Date of Patent: Mar. 7, 2017

(54) ***AECHMEA* PLANT NAMED 'AMERICA'**

(50) Latin Name: ***Aechmea dichlamydea* var. *trinitensis*×*Aechmea fendleri***
Varietal Denomination: America

(71) Applicant: Patricia Gomez Bullis, Princeton, FL (US)

(72) Inventor: Patricia Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 62 days.

(21) Appl. No.: 14/545,629

(22) Filed: May 29, 2015

(65) Prior Publication Data

US 2016/0353632 P1 Dec. 1, 2016

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — June Hwu
(74) *Attorney, Agent, or Firm* — C. A. Whealy

(57) ABSTRACT

A new and distinct cultivar of *Aechmea* plant named 'America', characterized by its upright and outwardly arching growth habit; unique creamy white, light green and green variegated leaves with green-colored margins and creamy white and light green-colored longitudinal stripes; inflorescences held upright and above the foliar plane on strong fuchsia red-colored scapes; tightly branched inflorescences with rosy-colored flower bracts with dark blue violet apexes; and long-lasting inflorescences.

1 Drawing Sheet

Botanical designation: *Aechmea dichlamydea* var. *trinitensis*×*Aechmea fendleri.*

Cultivar denomination: 'AMERICA'.

BACKGROUND OF THE INVENTION

The present invention relates to a new and distinct *Aechmea* plant, botanically known as *Aechmea dichlamydea* var. *trinitensis*×*Aechmea fendleri* and hereinafter referred to by the cultivar name 'America'.

The new *Aechmea* plant is a naturally-occurring whole plant mutation of the *Aechmea dichlamydea* var. *trinitensis*× *Aechmea fendleri* 'Blue Tango', disclosed in U.S. Plant Pat. No. 11,743. The new *Aechmea* plant was discovered and selected by the Inventor from within a population of plants of 'Blue Tango' in a controlled greenhouse environment in Princeton, Fla. in 2005.

Asexual reproduction of the new *Aechmea* plant by offsets in a controlled greenhouse environment in Princeton, Fla. since 2005 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'America'. These characteristics in combination distinguish 'America' as a new and distinct *Aechmea* plant:

1. Upright and outwardly arching growth habit.
2. Unique creamy white, light green and green variegated leaves with green-colored margins and creamy white and light green-colored longitudinal stripes.
3. Inflorescences held upright and above the foliar plane on strong fuchsia red-colored scapes.
4. Tightly branched inflorescences with rosy-colored flower bracts with dark blue violet apexes.
5. Long-lasting inflorescences.

Plants of the new *Aechmea* differ from plants of the parent, 'Blue Tango', primarily in leaf color as plants of 'Blue Tango' have solid green-colored leaves.

Plants of the new *Aechmea* can be compared to plants of *Aechmea fendleri* 'Blue Moon', not patented. Plants of the new *Aechmea* and 'Blue Moon' differ primarily in the following characteristics:

1. Plants of the new *Aechmea* and 'Blue Moon' differ in leaf color as plants of 'Blue Moon' have pale green to yellow-colored leaves.
2. Plants of the new *Aechmea* and 'Blue Moon' differ in flower bract color as plants of 'Blue Moon' have pale pink-colored flower bracts.
3. Plants of the new *Aechmea* and 'Blue Moon' differ in scape color as plants of 'Blue Moon' have pale pink-colored scapes.
4. Plants of the new *Aechmea* have longer-lasting inflorescences than plants of 'Blue Moon'.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color values cited in the detailed botanical description which accurately describe the colors of the new *Aechmea* plant.

The photograph on the right side of the sheet is a side perspective view of a typical flowering plant of 'America' grown in a container.

The photograph on the left side of the sheet is a close-up view of a typical inflorescence of 'America'.

DETAILED BOTANICAL DESCRIPTION

The aforementioned photographs and following observations, measurements and values describe plants grown in 20-cm containers during the winter and spring in a polypropylene-covered shadehouse in Princeton, Fla. During the production of the plants, day temperatures ranged from 28° to 30° C., night temperatures ranged from 18° C. to 22° C. and light levels ranged from 2,500 to 3,200 foot-candles. Plants were 15 months old when the photographs and description were taken. In the following description, color references are made to The Royal Horticultural Society Colour Chart, 2007 Edition, except where general terms of ordinary dictionary significance are used.

Botanical classification: *Aechmea dichlamydea* var. *trinitensis*×*Aechmea fendleri* 'America'.

Parentage: Naturally-occurring whole plant mutation of the *Aechmea dichlamydea* var. *trinitensis*×*Aechmea fendleri* 'Blue Tango', disclosed in U.S. Plant Pat. No. 11,743.

Propagation:

*Type*.—By offsets.

*Time to initiate roots, summer*.—About 30 to 45 days at temperatures ranging from 28° C. to 30° C.

*Time to initiate roots, winter*.—About 45 to 60 days at temperatures ranging from 28° C. to 30° C.

*Time to produce a rooted young plant, summer*.—About three months at temperatures ranging from 28° C. to 30° C.

*Time to produce a rooted young plant, winter*.—About six months at temperatures ranging from 18° C. to 22° C.

*Root description*.—Medium in thickness, fibrous; yellow and white in color, actual color will depend on substrate composition.

*Rooting habit*.—Moderately freely branching; medium density.

Plant description:

*Plant and growth habit*.—Upright and outwardly arching growth habit; rosette leaves are erect when young, becoming outwardly arching with development; plants readily produce offsets; vigorous growth habit.

*Plant height, soil surface to top of leaf canopy*.—About 87 cm.

*Plant height, soil surface to top of inflorescence*.—About 94 cm.

*Plant diameter or spread*.—About 106 cm.

Leaf description:

*Arrangement*.—Rosette, spiral phyllotaxis; leaves clasping; simple.

*Length*.—About 83.2 cm.

*Width*.—About 6.4 cm; at the base, about 11.5 cm.

*Shape*.—Lanceolate, strap-like.

*Apex*.—Cuspidate.

*Base*.—Truncate.

*Margin*.—Serrate and spinose.

*Aspect*.—Upright to arching with development.

*Texture, upper and lower surfaces*.—Smooth, glabrous; leathery; stiff.

*Luster, upper surface*.—Glossy.

*Luster, lower surface*.—Somewhat glossy.

*Venation*.—Parallel.

*Color*.—Developing leaves, upper surface: Towards the margins, 137B; central parallel longitudinal stripes, 144A to 144B and 145A to 145B. Developing leaves, lower surface: Towards the margins, 147B; central parallel longitudinal stripes, 145A to 145B and 145C. Fully expanded leaves, upper surface: Towards the margins, 146A; central parallel longitudinal stripes, 145A to 145B and 160A to 160B; venation, close to 146B and 145A. Fully expanded leaves, lower surface: Towards the margins, 146C; central parallel longitudinal stripes, 145A to 145B; venation, close to 146B and 145A.

Inflorescence description:

*Inflorescence form and arrangement*.—Long, open terminal panicles with tightly branched lateral panicles supported by erect and strong scapes; about 35 lateral panicles each with about 13 to 16 individual flowers; flowers distichous, sessile.

*Time to flower*.—Plants begin flowering about 12 to 16 weeks after planting.

*Inflorescence longevity*.—Inflorescences of the new *Aechmea* are very long-lasting, typically bract color will be maintained for about two months in the interior and about five months in the landscape depending on environmental conditions; inflorescences persistent.

*Fragrance*.—None detected.

*Inflorescence length*.—About 43.2 cm.

*Inflorescence width*.—About 21.5 cm.

*Flower buds*.—Length: About 1.9 cm. Diameter: About 6 mm. Shape: Ovoid, pointed. Texture: Smooth, glabrous. Color: Close to 93A; towards the base, close to 157A.

*Flower length*.—About 2.3 cm.

*Flower diameter*.—About 5 mm.

*Petals*.—Quantity and arrangement: Three in a single whorl. Length: About 2.3 cm. Width: About 3 mm. Shape: Elongated ovate to lanceolate. Apex: Acute. Base: Attenuate. Margin: Entire. Texture, inner and outer surfaces: Smooth, glabrous. Color: When opening, inner and outer surfaces: Close to N92B. Fully opened, inner and outer surfaces: Close to N92A.

*Sepals*.—Quantity and arrangement: Three in a single whorl. Length: About 1.9 cm. Width: About 6 mm. Shape: Elongated ovate to lanceolate. Apex: Apiculate. Base: Fused. Margin: Entire. Texture, inner and outer surfaces: Smooth, glabrous. Color: When opening and fully opened, inner surface: Close to 94B. When opening and fully opened, outer surface: Close to N92B.

*Primary bracts*.—Quantity and arrangement: One subtending each lateral panicle. Length, lower panicles: About 8 cm. Width, lower panicles: About 1.4 cm. Length, upper panicles: About 2.3 cm. Width, upper panicles: About 8 mm. Shape: Narrowly deltoid. Apex: Acuminate. Base: Truncate. Margin: Entire. Texture, inner surface: Smooth, glabrous. Texture, outer surface: Pubescent. Color, inner surface: Close to N79A. Color, outer surface: Close to 79A to 79B.

*Flower bracts*.—Quantity and arrangement: One per flower; subtending and closely appressed to the flower. Length: About 1.4 cm. Width: About 1 cm. Shape: Narrowly deltoid. Apex: Acuminate. Base: Truncate. Margin: Entire. Texture, inner and outer surfaces: Smooth, glabrous. Color, inner surface: Close to 86A, 86B and 86C. Color, outer surface: Towards the apex, close to N92A; towards the base, close to N79C.

*Scapes*.—Length, primary, to base of inflorescence: About 46 cm. Length, laterals: About 3 cm. Diameter, primary: About 1.2 cm. Diameter, laterals: About 5 mm. Strength, primary and laterals: Strong. Aspect, primary: Mostly upright. Aspect, laterals: Horizontal. Texture, primary and laterals: Tomentose, villose. Color, primary and laterals: Close to 185B to 185C.

*Reproductive organs*.—Stamens: Quantity per flower: Six. Filament length: About 1.3 cm. Filament color: Close to 75C to 75D. Anther length: About 4 mm. Anther shape: Elongated oval. Anther color: Close to 155B. Pollen: Scarce to none. Pollen color: Close to 155D. Pistils: Quantity per flower: One. Pistil length: About 2.5 cm. Style length: About 2.3 cm. Style color: Close to 195B. Stigma shape: Ovoid. Stigma color: Close to 91A. Ovary color: Close to 196D.

*Seeds*.—Seed production has not been observed on plants of the new *Aechmea*.

Temperature tolerance: Plants of the new *Aechmea* have been observed to tolerate temperatures ranging from about 3° C. to about 36° C.

Disease & pest resistance: Plants of the new *Aechmea* have been observed to be resistant to *Exserohelium*. Plants of the new *Aechmea* not been observed to be resistant to pests and other pathogens common to *Aechmea* plants.

It is claimed:

1. A new and distinct *Aechmea* plant named 'America' as illustrated and described.

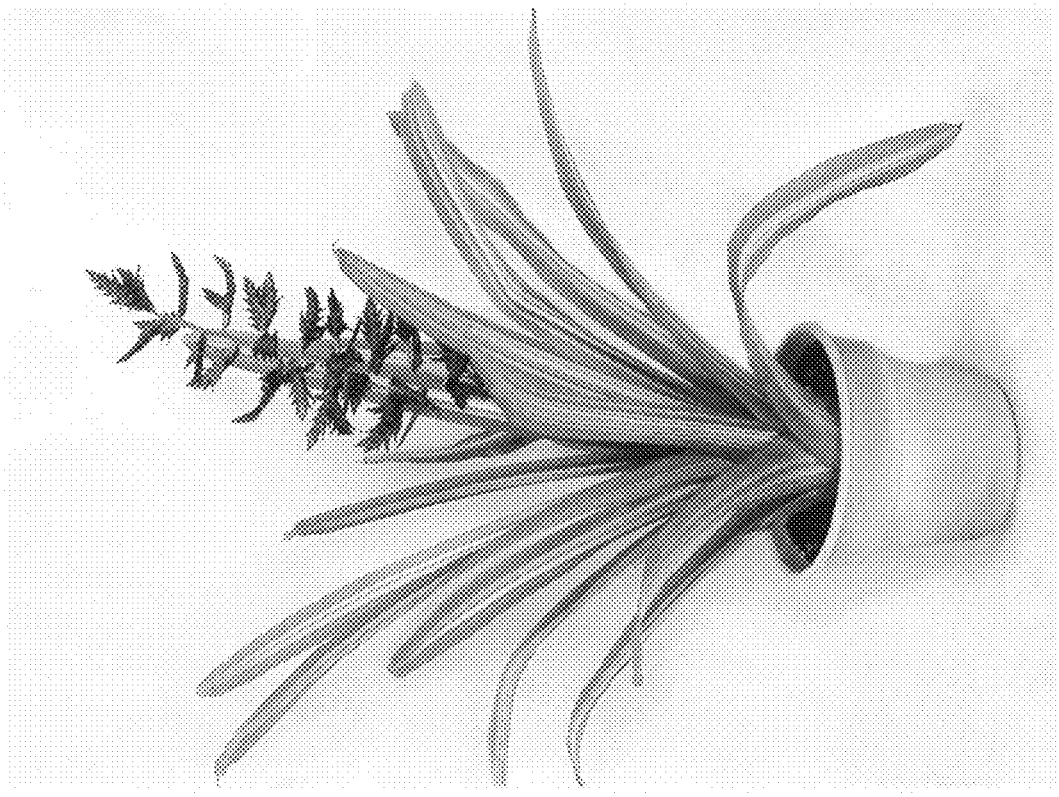
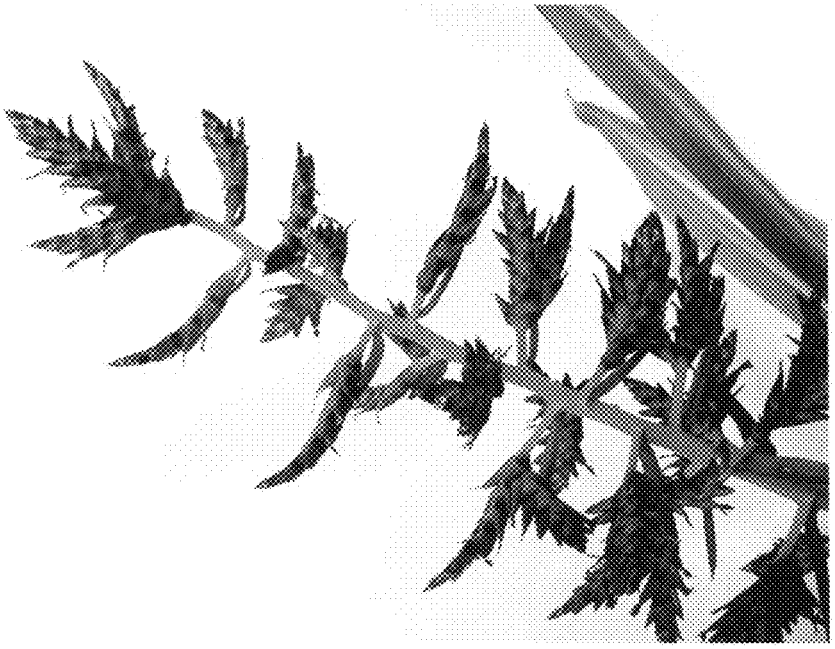

* * * * *